United States Patent [19]

Dryden et al.

[11] Patent Number: 4,838,258
[45] Date of Patent: Jun. 13, 1989

[54] GAS SAMPLING LUMEN FOR BREATHING SYSTEM

[75] Inventors: Paul E. Dryden, Indianapolis, Ind.; Richard J. Autieri, Hatfield, Pa.; Robert G. Daly, Indianpolis, Ind.

[73] Assignee: Gibeck-Dryden Corporation, Indianapolis, Ind.

[21] Appl. No.: 113,538

[22] Filed: Oct. 26, 1987

[51] Int. Cl.⁴ .................................... A61M 16/00
[52] U.S. Cl. .................. 128/204.18; 128/205.23
[58] Field of Search ............. 128/204.18, 911, 204.22, 128/205.23

[56] References Cited

U.S. PATENT DOCUMENTS

| | | |
|---|---|---|
| 3,163,707 | 12/1964 | Darling ...................... 128/204.18 X |
| 3,856,051 | 12/1974 | Bain . |
| 3,961,624 | 6/1976 | Weigl ............................ 128/205.23 |
| 4,007,737 | 2/1977 | Paluch ............................... 128/911 |
| 4,188,946 | 2/1980 | Watson et al. . |
| 4,281,652 | 8/1981 | Miller ............................ 128/911 X |
| 4,287,886 | 9/1981 | Thompson ................. 128/205.23 X |
| 4,320,754 | 3/1982 | Watson et al. . |
| 4,336,798 | 6/1982 | Beran ........................ 128/205.23 X |
| 4,462,397 | 7/1984 | Suzuki ............................ 128/911 X |
| 4,463,755 | 8/1984 | Suzuki ............................ 128/204.18 |
| 4,521,038 | 6/1985 | Cerny ........................ 128/204.18 X |
| 4,621,634 | 11/1986 | Nowacki et al. ................. 128/204.18 |
| 4,637,384 | 1/1987 | Schroeder ...................... 128/911 X |

FOREIGN PATENT DOCUMENTS 2013463 4/1970 France ............................... 128/911
2025239 1/1980 United Kingdom ................ 128/911

Primary Examiner—Gerald A. Michalsky
Attorney, Agent, or Firm—Woodard, Emhardt, Naughton, Moriarty & McNett

[57] ABSTRACT

A hose assembly for a breathing system has a corrugated flexible breathing hose with a first adaptor at one (machine) end of the hose for connection to an anesthesia machine remote from the subject patient using the hose for breathing. The adaptor has a cylindrical wall with a sampling port projecting laterally from the wall. A second adaptor is at the opposite (patient) end of the hose for connection to a breathing mask or endotracheal tube. A gas sample tube inside the hose has a sample entrance end projecting from the patient end adaptor a specified amount, extends through the entire length of the hose to the sampling port where it can communicate with a luer-lock connector and external sampling line to a gas sample monitor or, in another embodiment, the tube itself extends to the monitor. A resilient clip anchors the tube in a hose corrugation adjacent the patient end adaptor to fix the amount of extension of the sample tube from the patient adaptor and therefore fix its entrance end distance from the adaptor end. The tube is also anchored at the machine end adaptor. The tube is thick walled and relatively non-stretchable but loosely coiled inside the hose so it is not subjected to tensile loads when the corrugated hose is stretched linearly.

17 Claims, 3 Drawing Sheets

GAS SAMPLING LUMEN FOR BREATHING SYSTEM

TECHNICAL FIELD

The invention relates to breathing circuits, and particularly to conduits for taking gas samples from breathing circuits.

BACKGROUND ART

Taking gas samples from breathing circuits in anesthesia is a well known practice. It is desirable that the sample be taken at the patient. The sampling tube is one of several tubes associated with treatment of a patient. Being small and relatively fragile, the sampling tube is susceptible to damage by pinching or breakage. This is very detrimental when gas samples are relied upon for visual recognition and manual control, or for automatic control of administration of gases or other fluids.

Prior art U.S. Pat. Nos. 3,856,051 to Bain, 4,188,946 to Watson and Rayburn, and 4,320,754 to Watson and Rayburn disclose breathing devices in which a corrugated plastic breathing tube has a smaller tube extending lengthwise inside and terminating at the patient end for delivery of anesthetic gas to a patient. But to our knowledge, all gas sampling tubes used in the prior art are external to the breathing tubes.

DISCLOSURE OF INVENTION

In typical embodiments of our invention, a breathing hose has a tube inside it for obtaining gas samples. The sampling tube has a free inlet end protruding from the wye adaptor at the patient end of the hose. The tube is anchored at the adaptor to prevent extraction, so the free end location is properly established and maintained relative to the end of the adaptor for certainty and consistency of sampling gas adjacent or in a breathing mask or endotracheal tube, so the sample is reliably taken where desired relative to the patient airway. At the anesthetic gas machine end of the breathing hose, the disclosed embodiments have either of two types of treatment. One is termination of the sampling tube in a passageway at the external wall of the hose machine and adaptor for connection to a monitor sample line. The other treatment is continuation of the sampling tube through a wall port in the machine end adaptor and connection of the tube to the monitor itself. In still another embodiment of the invention, instead of a discrete inner tube, an inner lumen is provided in the hose, as extruded.

BEST MODE FOR CARRYING OUT THE INVENTION

Figure 1:
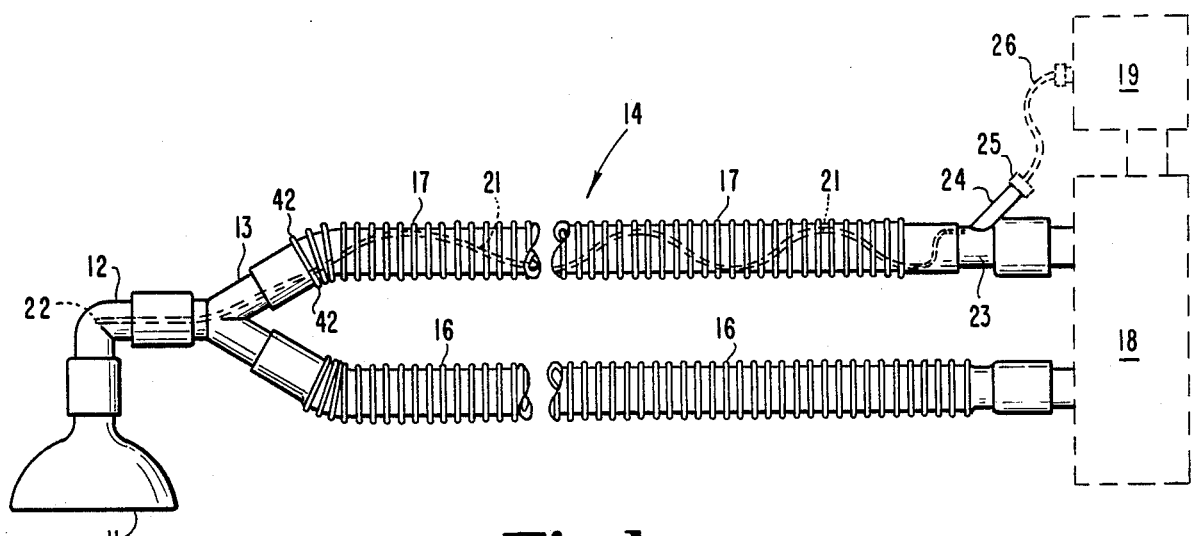
FIG. 1 is an elevational view, partially schematic, of a breathing system employing one embodiment of the present invention, where an internal sampling tube is used and terminated at the anesthetic gas machine end of a breathing hose in an adaptor fitting having a luer-lock type of sampling port for a remote sampling connection.

Referring to the drawings, a patient mask 11 is shown connected to an elbow 12, connected to a "bifurcated wye" 13 of the breathing hose assembly 14 which includes hoses 16 and 17 connectable directly or indirectly to the anesthetic gas machine 18 as shown in dotted lines. A gas sampling monitor 19 is shown mounted on top of the gas machine. The gas machine can be any of a variety well know and widely used. Similarly, the monitor can be any conventional monitor suitable for gas sampling. Some of the known brands are Sara, Perkin-Elmer, Datex and Puritan-Bennett, for example. Such components are known and used in either the open type or closed (circle absorption) type of breathing systems used in administration of anesthesia. The present invention is applicable to either type and includes the gas sampling feature which, in the embodiment of FIG. 1, includes the small sampling tube 21 inside the hose 17. This tube extends throughout the length of the hose 17 and through the wye adaptor 13 and elbow 12 to the sampling entrance end 22 of the tube, which is beyond the end of the adaptor and inside the mask adaptor elbow 12. Thus, it provides access to a gas sample precisely where it it desired. The other end of tube 21 in this embodiment is terminated in the adaptor 23 at the gas machine end of the hose assembly. It communicates with the luer-lock port 24 to which the external monitoring line 26 is connected by luer-lock nut 25 for conducting the gas sample from the tube 21 to the gas monitor 19 where line 26 is connected by nut 30. The tube 21, although relatively free inside the corrugated hose 17, is pushed into and attached securely by solvent bond in the tapered hole 23A (FIG. 3) in adaptor 23 so that there is a leak-proof communication through tube 21 from the sampling end 22 to port 24 whose interior 23B communicates with the hole 23A adjacent the machine end of tube 21. The patient end 22 of tube 21 is always in position to sample gases at the mask. In those cases where an endotracheal tube is used and attached to either the wye 13 or elbow 12, the end 22 of the sampling tube is in proper location for sampling gas in the endotracheal tube. The way this end 22 is held at the proper distance from the end of the wye adaptor is identical for both the FIGS. 1, 2 and the FIGS. 3, 4 embodiments, and will be described with reference to FIG. 3.

Figure 3:
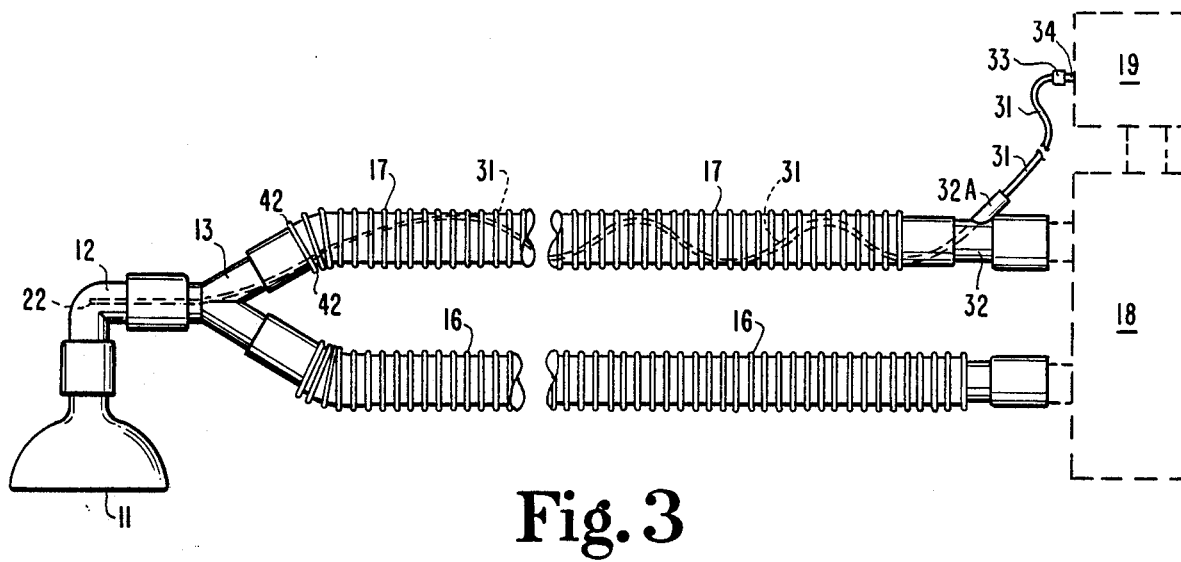
FIG. 3 is an illustration similar to that in FIG. 1 but showing a second embodiment of the invention wherein the internal sampling tube extends out of the breathing hose assembly and continues to a sample monitor where the tube is terminated in an end fitting which is connectable directly to the sample monitor.

Referring now to FIG. 3, where components identical to those of FIG. 1 are given the same reference numerals as in FIG. 1, the sampling tube 31 has its distal end 22 at the patient end of breathing hose 17 extending from that hose through the wye adaptor 13 and to a point 22 about 0.75 inches beyond the end of adaptor 13. But the other end, instead of terminating at fitting 23 like in FIG. 1, extends through the fitting 32 and is terminated with a luer-lock connector nut 33 which is connected to a luer-lock port 34 on the gas monitor 19. The overall length of tube 31 in this version is typically 10 feet to provide plenty of length outside hose 17 to reach a monitor wherever it will be located. The tube 31 is solvent bonded and perimetrically sealed at 35 in the lateral port 32A in adaptor 32.

Figure 2:
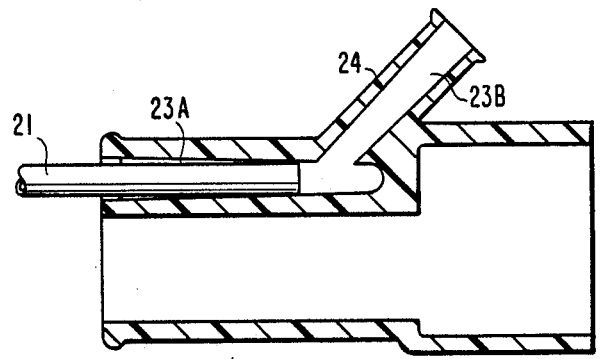
FIG. 2 is an enlargement of the adaptor fitting.
Figure 5:
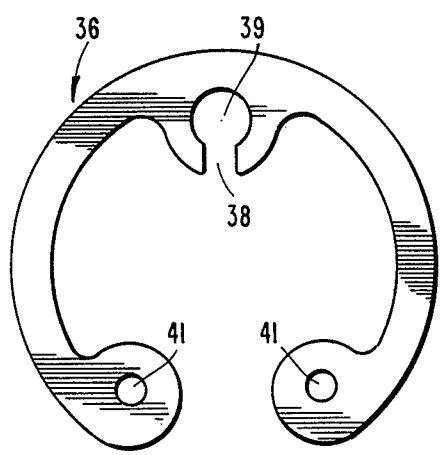
FIG. 5 is a face view of the sample tube retainer clip of both embodiments.
Figure 4:
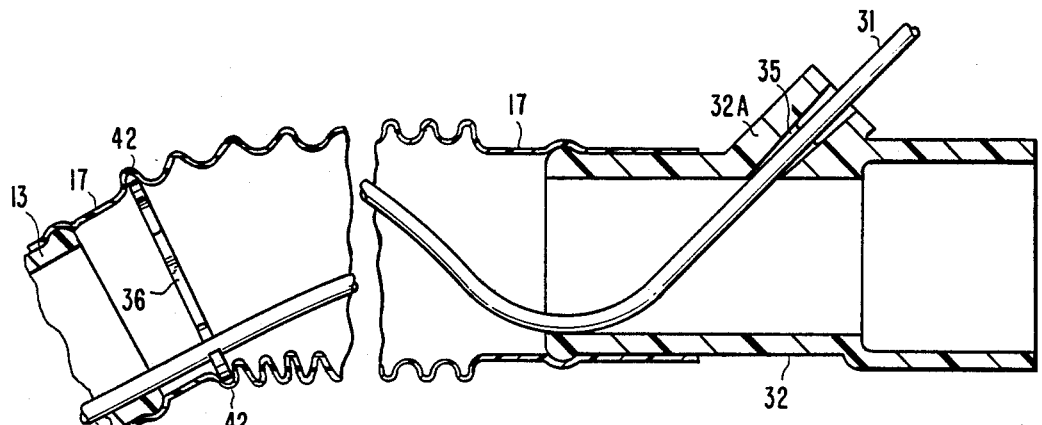
FIG. 4 is a view similar to FIG. 2 but is an enlarged section through the continuous sampling line adaptor of FIG. 3 at the machine end of the breathing hose, and through the tube anchoring point at the patient end wye adaptor.

It is a feature of our invention to fix and maintain a desired longitudinal position of sample entrance end 22 of tube 21 in FIGS. 1 and 2, and tube 31 in FIGS. 3 and 4. One anchoring system used in both embodiments is shown in FIG. 4. It includes a clip 36 which is located and resiliently confined in the patient end groove of the corrugated hose 17 and secures the tube 31 in position. Clip 36, better shown in FIG. 5 has a keyhole shaped notch with entrance slot 38 therein through which the tube 31 is pushed radially outward and received in the semi-circular hole 39 of the notch and securely retained therein, the slot having a width of about 0.0625 inch and the hole 31 having a diameter of 0.115 inch, in which the sample tube 31 with outside diameter of 0.112 inch is fit and solvent bonded to anchor the tube in the clip. The sample tube is made of transparent polyvinylchloride with inside diameter which may be 0.020, 0.031, 0.040, 0.047, 0.050 or 0.060 inch. The clip is made of Phillips K-resin material with tool receiver holes 41 in the ends of the clip whereby suitable pliers can be used to spring the ends toward each other and thereby constrict the clip so that it can be inserted in the clip receiving groove 42 in the hose 17 adjacent the wye adaptor 13. The clip expands snugly into groove 42 when the pliers are removed. It can also be solvent bonded in place if desired, but this is not necessary. With tube 31 anchored in the clip hole 39, and the clip 36 anchored in groove 42, although the tube 31 would otherwise be free to longitudinally move in the wye adaptor 13, the clip 36 prevents its axial movement therein.

By now it will be recognized that, in either embodiment of the invention, the tube 21 or 31 is anchored at both the patient end and machine end of hose 17. But the hose itself is standard thin wall 22 mm diameter corrugated of material which is 12% ethylvinylacetate blend with polyethylene. As such, it can be stretched longitudinally during handling and use. It is used for breathing hose 17 in lengths of 39, 48 or 60 inches. Tube 21 and tube 31 are made of clear polyvinylchloride thick wall and two inches longer than the hose, and arranged in a spiral or serpentine arrangement as shown, so the tube merely unwinds and or straightens to accommodate stretching of hose 17, without tensile loading the tube at either the patient end attachment clip or machine end attachment to the adaptor. The tube is made an additional inch longer where used with the 60 inch hose.

Figure 6:
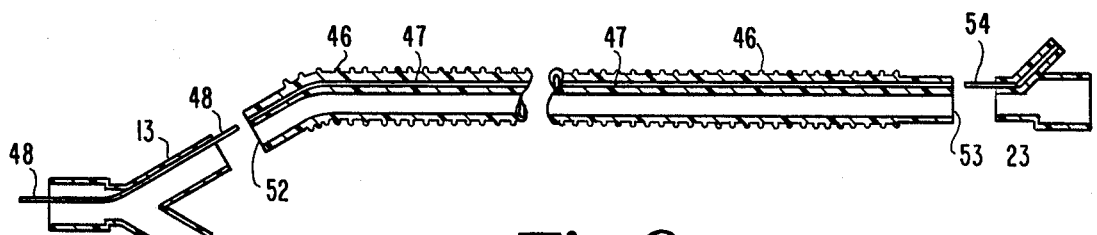
FIG. 6 is a longitudinal sectional, partially exploded, view showing a breathing hose with an integral internal lumen, and the patient end adaptor and the machine end adaptor with a luer-lock port.
Figure 7:
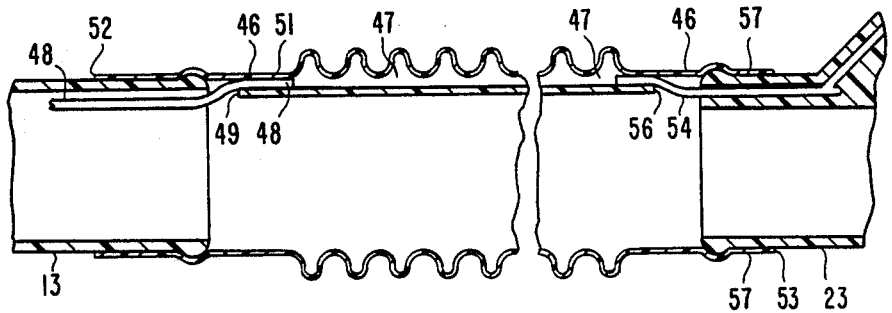
FIG. 7 is a fragmentary view of the assembly of FIG. 6 with enlargements of the portions where transition tubes at the patient end and the gas machine end of the hose are fitted into the integral gas sampling lumen in the breathing hose.

Referring now to FIG. 6, the adaptors 13 and 23 are the same as in FIG. 1, but the hose 46 is different in that the gas sampling provision is made by a lumen 47 integral with the hose and obtained in the wall of the hose as the hose is extruded. The hose is attached to the fittings 13 and 23 by solvent bonding in conventional manner, but communication with the sampling means at the patient end is provided by the patient end sampling tube 48 being inserted in the end of the lumen as shown in the enlargement of FIG. 7 where the tube 48 enters the lumen at 49 and is solvent bonded or heat sealed thereto at 51. That portion of the lumen which extended from the point 49 to the end 52 of the hose 46 can be slitted to the point 49 so it can be collapsed and fit around and be adequately heat or solvent sealed to the adaptor 13, while admitting the end of tube 48 into the lumen at the point 49.

Similarly, at the machine end 53 of hose 46, the lumen can be slitted to accommodate the transition tube 54 which enters the lumen at the edge 56 which may be the end of a slit in the lumen from that edge to the end 53, whereby the lumen portion from hose end 53 to the edge 56 can be slit and flattened to be fittingly and solvent bonded or otherwise sealed to the fitting 23 at 57.

Figure 8:
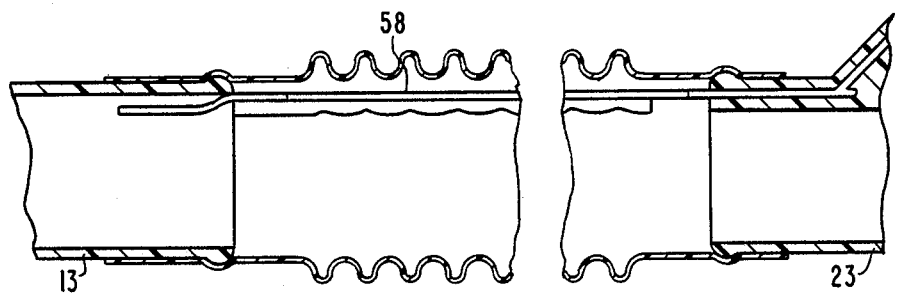
FIG. 8 is a view like FIG. 7 but showing a slightly different configuration of integral lumen.

Referring to FIG. 8, the features are all essentially the same as in FIG. 7 except that the inner wall of the lumen has somewhat the corrugated shape of the hose wall as shown at 58 and which it assumes during extrusion. Otherwise the connections are the same. Either the luer-lock port 24 of FIG. 2 or the tube through port 32A of FIG. 4 can be employed at the machine end as in FIG. 1 or FIG. 3, respectively.

Various materials can be used. The machine end adaptor 23 is typically made of polyvinylchloride. The patient end wye is made of polypropylene.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. In a breathing system, the combination comprising:
   a gas machine for providing inspiratory gas;
   a flexible breathing hose;
   first adaptor means at one end of the hose and coupled to said gas machine at a location remote from the subject using the hose for breathing, said first adaptor means having sampling port means as the wall thereof for passage of a gas sample therethrough;
   a breathing device to be attached to the subject;
   second adaptor means at the opposite end of the hose;
   gas sampler means for conducting a gas sample from beyond the said opposite end of the hose through most of the length of the hose to said sampling port means, said sampler means being located internally of the hose;
   a third adaptor means mounted to said second adaptor means and having said breathing device mounted to said third adaptor means;
   a gas sampling monitor;
   said sampler means having one end adjacent said breathing device and continuing through the inside of said hose and connected to said monitor to deliver gas samples from the breathing device to the monitor.

2. The assembly of claim 1 wherein:
   said port means include a luer-lock port, and said sampler means include a tube sealed and anchored at the luer-lock port and extending through said opposite end of the hose assembly and having a sampling end entrance beyond said opposite end.

3. The assembly of claim 2 and further comprising:

an elbow connected to said second adaptor means for connection to a breathing mask;

said tube being continuous from the luer-lock port to a point in said elbow whereby the sampling end entrance to said tube is positionable adjacent a breathing mask attached to said elbow.

4. The assembly of claim 1 wherein:

said sampler means includes a tube extending from inside said third adaptor means throughout the length of said hose and through said port means, said tube being anchored at said port means.

5. The assembly of claim 1 wherein:

said sampler means include a tube inside said hose;

said hose has a perimetrical inwardly opening groove adjacent said second adaptor means, the assembly further comprising a resilient clip received in said groove and having tube attachment means thereon for anchoring said tube at said second adaptor means;

said tube being continuous and extending continuously through said hose from a sampling input end outside of the hose assembly.

6. The assembly of claim 5 wherein:

said clip is a spring clip resiliently disposed in said groove, said tube attachment means including a keyhole slot therein with the base of the slot receiving and resiliently engaging said tube to prevent axial movement of said tube in said second adaptor means.

7. The assembly of claim 6 wherein:

said clip is horseshoe shaped, with tool receiver apertures therein, and said tube extends from said clip to a gas monitor.

8. The assembly of claim 7 wherein:

said hose has a nominal diameter of 22 mm, and said tube has an external diameter of at least 0.105 inches and is at least ten feet long from the sampling input end to a lure lock connector at said monitor.

9. The assembly of claim 1 wherein:

said gas sampler means includes a tube anchored at said second adaptor means.

10. The assembly of claim 9 wherein:

said hose is longitudinally flexible and stretchable;

said tube is laterally flexible but longitudinally less flexible and stretchable than said hose, said tube being disposed in a non-linear attitude inside said hose and in sufficient amount to change attitute in said hose during stretching of said hose to a maximum length of the hose without straightening all of said tube in said hose.

11. The assembly of claim 1 and wherein:

said second adaptor means is a wye adaptor, having a first arm to which said first hose is attached, and having a second arm;

a second breathing hose having one end attached to the second arm of said wye adaptor, said hoses having nominal diameters of 22 millimeters and having a nominal overall non-stretched length of at least 39 inches.

12. The assembly of claim 11 wherein:

said tube is anchored at said first adaptor means; and said sufficient amount of tube in between the location of anchorage in said hose and at said first adaptor means is about two inches more than said nominal overall length.

13. The assembly of claim 1 wherein:

said sampler means include a lumen formed in the wall of said hose and of material integral with the wall of the hose; and said sampler means further include one transition tube extending from beyond the end of said second adaptor means through said second adaptor means and into said lumen where it is secured and sealed to said lumen.

14. The assembly of claim 13 and further comprising:

another transition tube received in and sealed to said lumen at the said first adaptor means.

15. The assembly of claim 13 wherein said lumen has a smooth interior wall.

16. The assembly of claim 13 wherein said lumen has a corrugated inner wall matching the corrugation of the outer wall of said hose.

17. The assembly of claim 1 wherein:

said hose is made of a blend of ethylvinylacetate and polyethylene;

said first adaptor means is made of polyvinylchloride;

said second adaptor means is made of polypropylene; and said sampling tube is made of polyvinylchloride.

* * * * *